US006981502B2

(12) United States Patent
McCormick et al.

(10) Patent No.: US 6,981,502 B2
(45) Date of Patent: Jan. 3, 2006

(54) RESPIRATORY MASK HAVING INTRAORAL MOUTHPIECE WITH LARGE SEALING AREA AND MULTIPLE SEALING CONFIGURATION

(75) Inventors: James J. McCormick, Woodland Hills, CA (US); William Jou, West Hills, CA (US); David Anthony, North Hollywood, CA (US); David Isagholian, Marina Del Rey, CA (US)

(73) Assignee: Numask, Inc., Woodland Hills, CA (US)

( * ) Notice: Subject to any disclaimer, the term of this patent is extended or adjusted under 35 U.S.C. 154(b) by 0 days.

(21) Appl. No.: 10/816,702

(22) Filed: Apr. 1, 2004

(65) Prior Publication Data

US 2005/0217678 A1    Oct. 6, 2005

(51) Int. Cl.
A62B 18/08    (2006.01)
A62B 9/06     (2006.01)
A61M 16/00    (2006.01)
A61C 5/14     (2006.01)
A61B 19/00    (2006.01)

(52) U.S. Cl. .......................... 128/206.29; 128/200.26; 128/201.26; 128/207.14; 128/207.15; 128/859; 128/861; 128/863

(58) Field of Classification Search .......... 128/200.26, 128/201.26, 206.29, 207.14, 207.15, 859, 128/861, 863
See application file for complete search history.

(56) References Cited

U.S. PATENT DOCUMENTS

| | | | | | |
|---|---|---|---|---|---|
| 2,127,215 A | * | 8/1938 | Gwathmey | ............. | 128/207.14 |
| 2,669,988 A | * | 2/1954 | Carpenter | ................... | 128/861 |
| 2,705,959 A | * | 4/1955 | Elmore | .................. | 128/207.14 |
| 2,882,893 A | * | 4/1959 | Godfroy | ..................... | 128/861 |
| 3,013,554 A | * | 12/1961 | Safar et al. | ............ | 128/202.28 |
| 3,046,978 A | * | 7/1962 | Lea | ......................... | 128/205.13 |
| 3,306,298 A | * | 2/1967 | Raimo | ................... | 128/207.14 |
| 3,398,747 A | * | 8/1968 | Raimo | ................... | 128/207.14 |
| 3,419,004 A | * | 12/1968 | Berman | ................ | 128/207.14 |
| 3,576,187 A | * | 4/1971 | Oddera | ................... | 128/207.14 |
| 3,774,616 A | * | 11/1973 | White et al. | ........... | 128/200.26 |
| 3,908,665 A | * | 9/1975 | Moses | ................... | 128/207.14 |
| 3,926,196 A | * | 12/1975 | Bornhorst et al. | ..... | 128/207.14 |
| 3,930,507 A | * | 1/1976 | Berman | ................. | 128/207.14 |
| 4,112,936 A | * | 9/1978 | Blachly | ..................... | 128/861 |
| 4,198,970 A | * | 4/1980 | Luomanen | ............ | 128/207.15 |
| 4,270,531 A | * | 6/1981 | Blachly et al. | ........ | 128/207.14 |
| D261,442 S | * | 10/1981 | Anderson | .................. | D24/110 |
| 4,338,930 A | * | 7/1982 | Williams | ............... | 128/200.26 |
| 4,356,821 A | * | 11/1982 | Rind | ...................... | 128/207.14 |
| 4,365,625 A | * | 12/1982 | Rind | ...................... | 128/207.14 |
| 4,848,331 A | * | 7/1989 | Northway-Meyer | ... | 128/200.26 |

(Continued)

*Primary Examiner*—Henry Bennett
*Assistant Examiner*—Nihir Patel
(74) *Attorney, Agent, or Firm*—O'Melveny & Myers LLP

(57) ABSTRACT

A respiratory mask provides improved sealing through the use of an intraoral mouthpiece with a large sealing area. A tubular extension, configured at one end to accept standard respiratory fittings, is the conduit for gas delivery to the intraoral mouthpiece. The respiratory mask may also include an intraoral oropharyngeal airway which flexes so that it can be inserted without the need for rotation or use of a tongue blade. The respiratory mask may also include an external shield to enhance sealing and provide a barrier of protection for the healthcare provider. The mask's design allows for a novel handgrip technique that allows a single healthcare provider to ventilate with enhanced sealing.

36 Claims, 11 Drawing Sheets

U.S. PATENT DOCUMENTS

| | | | |
|---|---|---|---|
| 4,877,024 A * | 10/1989 | Sheehy | 128/207.14 |
| 4,919,126 A * | 4/1990 | Baildon | 128/207.14 |
| 5,205,281 A * | 4/1993 | Buchanan | 128/207.14 |
| 5,279,610 A * | 1/1994 | Park et al. | 606/108 |
| 5,355,874 A * | 10/1994 | Bertram | 128/200.26 |
| 6,196,224 B1 * | 3/2001 | Alfery | 128/207.14 |
| 6,474,332 B2 * | 11/2002 | Arndt | 128/200.26 |
| 6,536,424 B2 * | 3/2003 | Fitton | 128/200.24 |
| 6,606,991 B2 * | 8/2003 | Chou | 128/200.26 |
| D479,876 S * | 9/2003 | Gradon et al. | D24/110.5 |
| 6,675,804 B1 * | 1/2004 | Pivovarov | 128/848 |
| 2002/0139375 A1 * | 10/2002 | Kulick | 128/848 |

* cited by examiner

RESPIRATORY MASK HAVING INTRAORAL MOUTHPIECE WITH LARGE SEALING AREA AND MULTIPLE SEALING CONFIGURATION

BACKGROUND OF THE INVENTION

1. Field of the Invention

The present invention relates to devices used to aid in and provide ventilation and more particularly to respiratory masks having intraoral mouthpieces to provide improved sealing to a wearer.

2. Description of Related Art

Respiratory masks are commonly used in emergency care and critical care situations. They may be used in conjunction with bag valves to deliver gases under positive pressure to a patient not capable of adequately breathing independently. Respiratory masks, in conjunction with a one-way valve, are also used by rescuers to provide mouth-to-mask resuscitation to a person who is not breathing. Additionally, respiratory masks are used in conjunction with bilevel positive airway pressure and continuous positive airway pressure machines to aid respiration in certain instances.

The traditional respiratory mask includes a fixed domed or cup-shaped device that fits over the mouth and nose of a wearer. The edge of this dome or cup fits against the face of the wearer. Air or another gas or mixture of gases is introduced into the traditional mask through an opening that is typically at the peak of the dome or cup. The integrity of the seal between the edge of the traditional respiratory mask and the face of the wearer is critical to the gas delivery effectiveness of a traditional respiratory mask. While commonly used in the healthcare industry, these masks have several serious shortcomings.

Healthcare providers must have access to several sizes of traditional respiratory masks for use on people of different ages and facial sizes. This need for access to several different sized masks is particularly burdensome to emergency medical technicians who must transport medical supplies in a limited amount of space. Therefore, to ease this burden on emergency medical personnel, an improved respiratory mask would be wearable by a large portion of the population regardless of age or face size.

Perhaps the largest shortcoming of the traditional sized respiratory masks is that despite the availability of several sizes of mask, the wide variations in facial features among people prevent these masks from sealing effectively. Where the person to be ventilated has facial hair, traditional respiratory masks are almost completely incapable of forming a seal with the person's face. This deficient sealing causes leakage around the edges of the mask and significantly decreased gas delivery efficiency. The traditional respiratory masks frequently leak near the nasal bridge section of the mask, leading to drying of the cornea and ultimately keratitis.

An inherent problem with traditional respiratory masks that contributes to gas leakage is that the gas must pass from the mask through the lips and teeth of the person being ventilated before being received in the person's mouth, or it must pass through the nose of the person being ventilated. The lips and teeth are resistance points that disrupt the laminar flow of the gas, leaving the incomplete seal around the edge of the mask as a path of least resistance from which the gas leaks. Likewise the nasal passages are narrow, with turbinates to disrupt flow in addition to inherent mucous and debris accumulation, thereby providing a restrictive, non-laminar flow circuit.

Where a bag valve is used, it optimally requires two healthcare providers to effectively ventilate a person. It requires both hands of one of the healthcare providers to hold the respiratory mask and apply pressure onto the face of the person to be ventilated in an attempt to seal the mask, while another healthcare provider squeezes the bag. Such an arrangement is highly disadvantageous for long term ventilation of a person, such as occurs when a patient is transported or under anesthesia in an operating room. Healthcare providers using these traditional respiratory masks will often attempt to compensate for the deficient seal by either applying excess pressure to the mask onto the face of the person being ventilated or, in the case of a bag valve, by squeezing the bag with maximal intensity. The application of excessive pressure by the healthcare provider on a traditional respiratory mask is problematic for several reasons. The pressure required to be applied for proper sealing of the face mask can quickly lead to healthcare provider fatigue. A fatigued healthcare provider may be less able to apply sufficient pressure onto the traditional respiratory mask to reduce its inherent leakage and may have difficulty performing this and other critical tasks. Additionally, the application of excessive pressure to a traditional respiratory mask onto the face of the person being ventilated will cause the mask to develop pressure points on the bridge of the nose, cheek bones, and chin. This pressure could lead to irritation of wearer's face and discomfort or pain to the wearer.

Proper head and neck position. i.e. neck extension, and maneuvers such as the chin-lift and jaw-thrust are also required for efficient ventilation by opening and maximizing the patency of the airway. These tasks, in addition to the above task of preventing leaks can overwhelm the healthcare provider and often require two providers to ventilate a patient adequately.

Squeezing the bag with maximal intensity in an attempt to compensate for deficient sealing of a traditional respiratory mask is likewise problematic. The increased inspiratory forces may exceed the opening pressure of the esophagus, possibly leading to esophageal and gastric dilatation and subsequent aspiration.

Clearly, there is a need for an improved respiratory mask addressing the shortcomings of the traditional respiratory mask. Others have attempted to address the problems with traditional respiratory masks. Their attempted solutions, however, have fallen far short of addressing all of the problems of the traditional respiratory mask and have created new problems.

Several attempts at improving the traditional respiratory mask have done so through the use of a gas delivery tube feeding into an intraoral mouthpiece with a bite block. An intraoral mouthpiece eliminates one shortcoming of traditional respiratory masks: the reliance on a nearly impossible to achieve seal between the mask and the outside of the mask wearer's face. Intraoral mouthpieces also bypass the mask wearer's lips, which posed a source of resistance to flow and disruption of laminar flow to traditional respiratory masks. Nevertheless, despite these advantages over the traditional respiratory masks, the integration of a bite block into the design creates several disadvantages.

Mouthpieces having bite blocks or bite plates cannot be safely inserted into the mouth of someone who is combative, semiconscious, or having a seizure. A healthcare provider attempting to insert a mouthpiece with a bite plate by prying open the jaws of a person to be ventilated would do so at risk of sustaining bite related injuries, possibly as severe as amputation of a digit or contracting an infectious disease. Forced insertion of a mouthpiece with bite block into the mouth of a person to be ventilated also risks the person's aspiration of blood, teeth, dental fragments, or fragments of the bite block broken off during insertion. Another disadvantage of mouthpieces with bite blocks is that their wearers will reflexively bite down and typically they may not be worn by persons with missing teeth, dentures, or those with facial injuries, jaw trauma or fractures. Further, because people wearing mouthpieces with bite blocks will bite down on the blocks, the use of these mouthpieces can quickly lead to jaw fatigue and discomfort. These bite blocks may also stimulate a gag reflex and increase the aspiration risks in the awake or semiconscious patient.

The integration of a mouthpiece having a bite block with an intraoral oropharyngeal airway presents additional disadvantages. Intraoral oropharyngeal airways are used to prevent the tongue of the person to be ventilated from blocking the airway while providing a direct path for gas delivery to the pharynx. Intraoral oropharyngeal airways are typically inserted either by rotating the oropharyngeal airway 180° as it is inserted or by using a tongue blade. If the oropharyngeal airway is to be integrated with the mouthpiece, it would be impossible for the airway to be inserted with a 180° rotation method as the bite block would collide with the teeth of the person to be ventilated. A tongue blade, which would need to be carried by an emergency healthcare provider such as an emergency medical technician, would be necessary to insert the intraoral oropharyngeal airway. Therefore, the integration of a mouthpiece with a bite block is also undesirable.

Additionally, while intraoral mouthpieces with incorporated bite blocks address the problem of gas delivery to the mouth of a person, they can create gas leakage through the nose of the person to be ventilated. The prior art respiratory devices having intraoral mouthpieces with bite blocks deliver gas to the mouth of a person to be ventilated without providing for sealing the nose of the person to be ventilated. Standard nose occluding clips could be used to close the nostrils of a person being ventilated with an intraoral mouthpiece with bite block, but this solution would require a healthcare provider to have access to nose occluding clips. During ventilation with an intraoral mouthpiece, large volumes of otherwise delivered gas will escape through the nose of the person being ventilated. Therefore, it is desirable for an intraoral respiratory mask to include an integrated nose clamp.

While the respiratory mouthpieces with bite blocks do address several problems of the traditional respiratory mask, the bite blocks make these devices impossible to use on certain individuals (with dentures, missing teeth, or facial/jaw trauma), dangerous to use on others (combative or semiconscious), and uncomfortable to use on everyone. Moreover, since prior art intraoral mouthpieces with bite blocks do not address gas leakage from the nose of the person to be ventilated, they are still inefficient gas delivery devices. Lastly, none of the mouthpieces with bite blocks can accommodate typical oropharyngeal airways.

There have been attempts to address the problems of the traditional respiratory masks without using a bite block or bite plate. But, these attempts also create problems. For example, there are also prior art intraoral mouthpieces featuring a conduit that is flanged on one end. The flanged end is to be placed between the lips and gums of the person to be ventilated. A healthcare provider would ventilate the person with the flanged conduit device by exhaling through the conduit. The flanged mouthpiece, while likely an improvement over the traditional respiratory mask, has serious wear and comfort issues. The intraoral flanged portion of the device extends just above and below the gum-line in the person to be ventilated. Also, the flanged end does not extend posteriorly or laterally in the mouth of the person to be ventilated beyond the front teeth. Therefore, while the flanged end of the device provides a seal between the material of the flanged end and the inside of the lips and gums of the person to be ventilated, that seal still leaves avenues for gas leakage. With the flanged conduit respiratory device, air may leak around the flanged end at the top and bottom (between the flanged end and the gums above and below the gumline of the person to be ventilated) and the sides (towards the canine teeth and molars of the person to be ventilated).

A further shortcoming of the flanged conduit respiratory device is that the flanged end of the conduit does not lie flush to the teeth and gums of the person to be ventilated. Rather, the flanged end has an arcuate profile designed to mate with the inside of the lips of the person to be ventilated. Thus, only the material nearest the edge of the flanged end actually forms a seal with the mouth of the person to be ventilated. This limited sealing area will result in a pressure concentration, irritation, and discomfort on the gums of the person to be ventilated, possibly leading to lacerations and bleeding. Therefore, while the flanged conduit respiratory device is an attempt to address the problems of the traditional respiratory mask, it suffers the disadvantages of inadequate intraoral sealing due to a small seal surface area and gum irritation or injury to the wearer. Further, there is no nasal occlusive component and the device is incompatible with an oropharyngeal airway.

Another prior art approach to address the problems of the traditional respiratory mask uses an inflatable intraoral seal bladder attached to an intraoral mouthpiece and a conduit. Though the inflatable seal rests in the space between the gum and the inner lips of the wearer, air/gas can still escape around it when no external pressure is applied to the face and lips of the wearer. In addition, the inflatable seal may cause pressure points and irritate the gum and mucosa of the wearer. The inflatable seal approach is also undesirably complex, requiring inflation of both an intraoral seal and a separate nasal block before use, and this complexity necessitates several component elements that are in danger of being bitten off and rendered ineffective by a combative or semi-conscious person. Time, which is very limited in a critical or emergent resuscitation, is also required to inflate both the intraoral seal and the nasal block. This device is also incompatible with current oropharyngeal airways.

As is evidenced by the above discussion of the related art, there is a need for an improved respiratory mask with improved sealing and gas delivery capability that can be safely inserted in mouths of combative and semiconscious persons and that is comfortable for people to wear. The improved respiratory mask should also allow a single healthcare provider to ventilate a person without significant gas leakage. It must also allow for the use of an oropharyngeal airway, when one is needed, to ensure a patient airway.

SUMMARY OF THE INVENTION

The present invention addresses the shortcomings of the prior art, by providing a respiratory mask having improved sealing that can be comfortably worn and that can be effectively sealed and used by a single healthcare worker.

The respiratory mask of the present invention has at its core an intraoral mouthpiece configured to take advantage of the natural seals existing between the gums and inside of the lips of persons to be ventilated. Thus, the respiratory mask of the present invention does not rely on sealing to the surface of the face of the wearer. Moreover, the intraoral mouthpiece of the present invention has no integrated bite block. Therefore, the respiratory mask of the present invention may be worn by combative and semi-conscious people as well as people with missing teeth or those with jaw or facial trauma.

The main component of the intraoral mouthpiece is a sheet of flexible material shaped to conform to the inner surface of the lips and gums of a person. The upper and lower edges of the intraoral mouthpiece extend past the gumlines almost to the terminus of the cavities between the lips and gums of the person to be ventilated. The intraoral mouthpiece is bowed and its side edges extend posteriorly in the mouth of the person to be ventilated to a depth past the front teeth. Preferably, the side edges of the intraoral mouthpiece extend posteriorly to a minimum depth of the second premolar. The surfaces of the intraoral mouthpiece are substantially parallel to the teeth and gums of the person to be ventilated. The intraoral mouthpiece of the present invention, therefore, seals to a large area of the lips and gums of the wearer. Advantageously, this large area seal both enhances sealing for increased gas delivery efficiency and reduces pressure concentration on the gums of the wearer while eliminating irritation, discomfort, and injury.

In addition to the large sealing surface area, the intraoral mouthpiece has several features that address the problem of maintaining wearer comfort. The surfaces of the intraoral mouthpiece that contact the lips and gums of the person to be ventilated are substantially smooth with rounded edges. Further, a top portion of the intraoral mouthpiece is offset from a bottom portion of the mouthpiece in the anterior-posterior plane. This offset allows the mouthpiece to seal in the mouths of persons with the more common overbite, or, by rotating the mouthpiece 180°, to seal in the mouths of persons with underbites. Additionally, the intraoral mouthpiece may have at least one notch centered at its upper or lower edge. The notches prevent the intraoral mouthpiece from irritating the frenula between the lips and gums of the person to be ventilated. The flexible material of the intraoral mouthpiece will allow the intraoral mouthpiece to mold to the irregularities of the teeth and gum to minimize holes for air/gas escape.

Unlike the extreme variability among people in size and placement of nose, cheek bones, and chin, the dimensions of the inner lips and gums are relatively fixed among people from a young age. Therefore, advantageously, an emergency healthcare provider need not carry many sizes of the respiratory mask of the present invention to be able to ventilate people of various ages and sizes.

The intraoral mouthpiece has a central orifice for gas delivery. The central orifice feeds into a tubular extension. The tubular extension has a reinforced collar at the end near the intraoral mouthpiece. This reinforced collar allows a healthcare provider to handle and position the respiratory mask of the present invention and also allows the healthcare provider to enhance the sealing of the mask using a novel single-hand handgrip technique. When the mouth of the person to be ventilated is closed around the reinforced collar of the tubular extension, the jaw of the person to be ventilated remains slightly agape due to the vertical height of the intraoral component. Therefore, the lips and the teeth of the person to be ventilated are not obstacles to gas delivery with a respiratory mask of the present invention. The tubular extension is configured to accept standard respiratory fittings at the end opposite the intraoral mouthpiece. The respiratory mask of the present invention may be used in conjunction with a bag valve for bag valve ventilation, with a one-way valve for mouth-to-mask ventilation, or with a ventilator for bilevel positive airway pressure or continuous positive airway pressure ventilation. The tubular extension may also feature a port to allow for a pressure relief valve, a $CO_2$ monitor, or other devices.

The respiratory mask of the present invention may also comprise an intraoral oropharyngeal airway to provide a direct conduit for air or gas into the pharynx of the person being ventilated while preventing the person's tongue from blocking the airway. The intraoral oropharyngeal airway of the present invention is a gently curved tube featuring at least one row of notches, or similar configuration to enhance flexibility, to allow it to flex inferiorly and follow the oral palate of the person to be ventilated during insertion. Therefore, the intraoral oropharyngeal airway of the present invention can be inserted without a 180° rotation of the respiratory mask and without the use of a tongue blade. Two embodiments of intraoral oropharyngeal airway are contemplated within the scope of the present invention. In the first embodiment, one end of the intraoral oropharyngeal airway mates with a recess in the inner wall of the intraoral mouthpiece. In a second embodiment, the intraoral oropharyngeal airway is slidably inserted through the tubular extension. This slidably inserted intraoral oropharyngeal airway protrudes outside the tubular extension of the respiratory mask and is configured to accept standard respiratory fittings.

To enhance the sealing of the respiratory mask of the present invention and provide a barrier of protection to the healthcare provider, the respiratory mask may additionally comprise an external shield. The external shield and intraoral mouthpiece may be integrated as a single unit, or alternatively, the external shield may be a separate piece configured to slide over the tubular extension of the respiratory mask. Where the external shield is a separate piece, it may have a multi-position locking mechanism allowing the position of the external shield relative to the intraoral mouthpiece to be adjusted and secured. This multi-position locking mechanism allows the external shield to be securely positioned to accommodate the wide variations in lip and surrounding tissue thicknesses among people. The external shield is preferably translucent so that the healthcare provider can visualize vomit or blood or other causes for aspiration of the person to be ventilated. Additionally, the external shield may have slits to accommodate restraining straps. The use of restraining straps to hold the respiratory mask to the face of the person to be ventilated allows a single healthcare provider to ventilate a person without becoming fatigued—a clear improvement over the prior art.

The external shield also addresses the problem of gas leakage from the nose of the person to be ventilated. Embodiments of the external shield comprise a nasal clamp affixed to the portion of the external shield lying adjacent to the nose of the person to be ventilated. Several types of nasal clamp are contemplated within the scope of the present invention. A first nasal clamp comprises two flaps and an adjustable reinforcement member such as a malleable band, ratcheted clamp, or other similar device. Each of the two flaps lies adjacent to a nostril of the person to be ventilated. The adjustable reinforcement member reinforces the two flaps and allows the flaps to maintain a new orientation. For example, the malleable band allows the nasal clamp to occlude and maintain pressure on the nostrils of the person being ventilated when squeezed together. A second type of nasal clamp within the scope of the present invention is a partial nasal mask extending from the portion of the external shield lying adjacent to the nose of the person to be ventilated. The partial nasal mask extends approximately half way up the nose of the person to be ventilated. The partial nasal mask further comprises padding and an adjustable reinforcement member such as a malleable band, ratcheted clamp, or other similar device. The padding provides comfort to the wearer of the respiratory mask and also applies pressure to close the nostrils of the person to be ventilated. The adjustable reinforcement member reinforces the partial mask and allows the mask to maintain a new shape when a healthcare provider applies pressure on the nasal mask to seal the nostrils of the person being ventilated. The nasal clamp enables a single healthcare provider to ventilate a person without becoming fatigued as the healthcare provider may seal the nose of the person by squeezing the nasal clamp to seal the nostrils of the person, then allow the adjustable reinforcement member to maintain pressure on the nostrils.

Several embodiments of external shield are contemplated within the scope of the present invention. In one embodiment, the external shield is a substantially rectangular sheet of material that extends from approximately the chin of the person to be ventilated to just below the nose of the person to be ventilated. In another embodiment, the external shield is an invertible domed face shield with padding. The invertible domed face shield is substantially oval to fit over the mouth of the person to be ventilated. The invertible domed face shield has padding around its edges to seal against the face of its wearer. This padding may be grooved or coated with a sticky substance to improve sealing on faces of people with facial hair or whose faces may be coated with blood or other fluids. The invertible domed face shield may be inverted away from the face of the person to be ventilated while the intraoral mouthpiece of the respiratory mask is being inserted into the person's mouth, then inverted back to seal around the face of the person to be ventilated. The inverted dome face shield could apply the needed pressure onto the face of the wearer to prevent air/gas from escaping around the intraoral mouthpiece and out the lips or nose. Additional pressure, if needed, can be provided by the healthcare provider by applying pressure onto the face shield with the use of a hand or restraining strap.

As is evident to persons having ordinary skill in the art, multiple embodiments of respiratory masks within the scope of the present invention are contemplated by combining the various embodiments of the intraoral mouthpiece, intraoral oropharyngeal airways, external shields, and nasal clamps.

A novel handgrip technique within the scope of the present invention allows a single healthcare provider to provide ventilation to a person with a respiratory mask of the present invention without the use of an external shield. To perform the technique, the healthcare provider first inserts the respiratory mask's intraoral portion into the mouth of the person to be ventilated. The healthcare provider then positions one hand in a "u" shape with the palm cradling the chin of the person being ventilated and the thumb and fingers positioned on either side of the nose of the person being ventilated. The healthcare provider applies pressure with the hand onto the face of the person. Note that unlike the traditional respiratory mask where excessive pressure must be applied to seal a small edge of the mask onto the face of the person, with the mask of the present invention, only a small amount of pressure is required to seal the intraoral mouthpiece with the lips and gums of the person and this pressure is distributed over a relatively large area. Therefore, advantageously, wearer discomfort due to pressure concentrations does not occur with the handgrip technique of the present invention. Also, with the healthcare provider's hand and palm cradling the wearer's chin, the person can help to extend the head and neck to aid in opening the wearer's airway. The healthcare provider can also simultaneously apply pressure to seal the nostrils of the person by squeezing the nose of the person between the thumb and at least one finger. The healthcare provider can then relax the pressure on the nostrils while the person being ventilated is exhaling, allowing gas to escape from the nose of the person. The handgrip technique of the present invention, therefore, allows the healthcare provider to seal the nose and mouth of the person being ventilated with a single hand, freeing the other hand to properly squeeze a bag for bag valve ventilation. Also, by using the novel handgrip technique, the healthcare providers should be able to more correctly position the patient's airway and head. The previous art, due to its limitations in frequently requiring two hands for proper application, frequently impeded a single provider's ability to move the patients head into the proper hyperextended position.

DETAILED DESCRIPTION OF THE INVENTION

The present invention provides a respiratory mask that overcomes the limitations of prior-art respiratory masks. In the detailed description that follows, like element numerals are used to indicate like elements that appear in one or more of the drawings.

Figure 1:
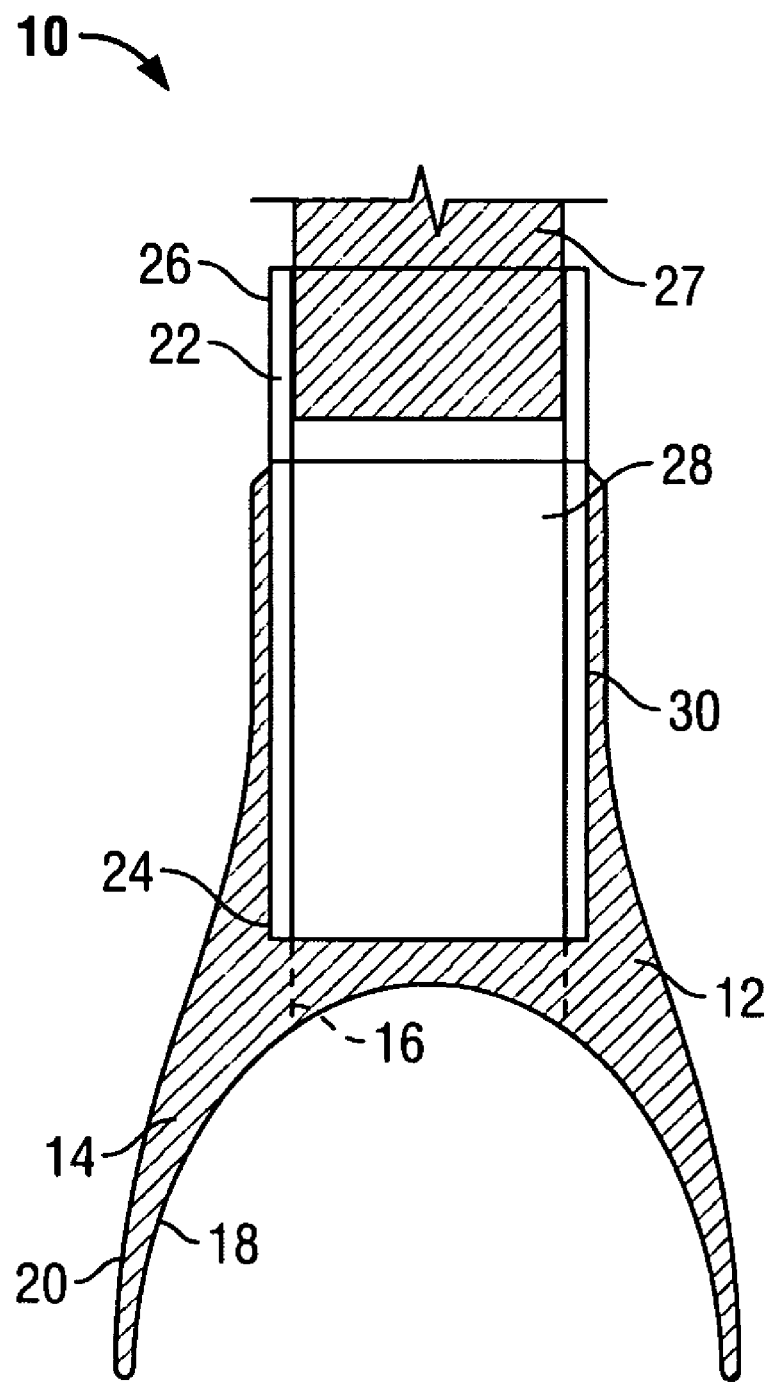
FIG. 1 is a cross-sectional top-view diagram showing a respiratory mask of the present invention.

A cross-sectional top-view of the respiratory mask 10 according to an embodiment of the invention is shown in FIG. 1. In overview, the respiratory mask 10 is comprised of a tubular extension 22, a reinforced collar 30, and an intraoral mouthpiece 12.

The intraoral mouthpiece 12 further comprises a substantially oval and bowed sheet of material 14 and a central orifice 16 through the substantially oval and bowed sheet of material. The substantially oval and bowed sheet of material 14 has an inner surface 18 and an outer surface 20. The central orifice 16 is substantially centrally located in the both the horizontal and vertical axes of the sheet of material 14. The central orifice 16 provides a passage between the outer surface 20 of the sheet of material 12 and the inner surface 18 of the sheet of material 14. The inner surface 18 and the outer surface 20 of the sheet of material 14 may be substantially smooth to reduce any pressure points and possible sources of irritation in the mouth of the ventilated person. The intraoral mouthpiece 12 of the present invention may be composed of plastic, rubber, silicon, or similar flexible material. The intraoral mouthpiece, advantageously, distributes its sealing over a large surface area while maintaining wearer comfort. Further, the intraoral mouthpiece's placement behind the lips of the person to be ventilated removes the lips as an obstacle to gas delivery.

The tubular extension 22 has a proximal end 24, a distal end 26, and a conduit 28. At the proximal end 24 of the tubular extension 22, the conduit 28 of the tubular extension 22 feeds into the central orifice 16 of the intraoral mouthpiece 12. In an embodiment of the present invention, the central orifice 16 has a substantially oval shape, and the conduit 28 of the tubular extension 22 has a cross-section that tapers from a substantially circular shape at its distal end 26 to a substantially oval shape at its proximal end 24. In an embodiment of the present invention, the distal end 26 of the tubular extension 22 is composed of hardened plastic configured to hold firmly to standard respiratory fittings 27 for a bag valve mask or demand valve. Therefore, the respiratory mask of the present invention may be used in conjunction with a one-way valve for artificial ventilation (or mouth-to-mask ventilation), with a bag valve for bag valve ventilation, or with a ventilator for bilevel or continuous positive airway pressure ventilation.

The reinforced collar 30 surrounds the tubular extension 22 and extends from the proximal end 24 of the tubular extension 22 part way to the distal end 26 of the tubular extension 22. The reinforced collar 30 allows the respiratory mask to be sealed with a unique handgrip technique.

Figure 2:
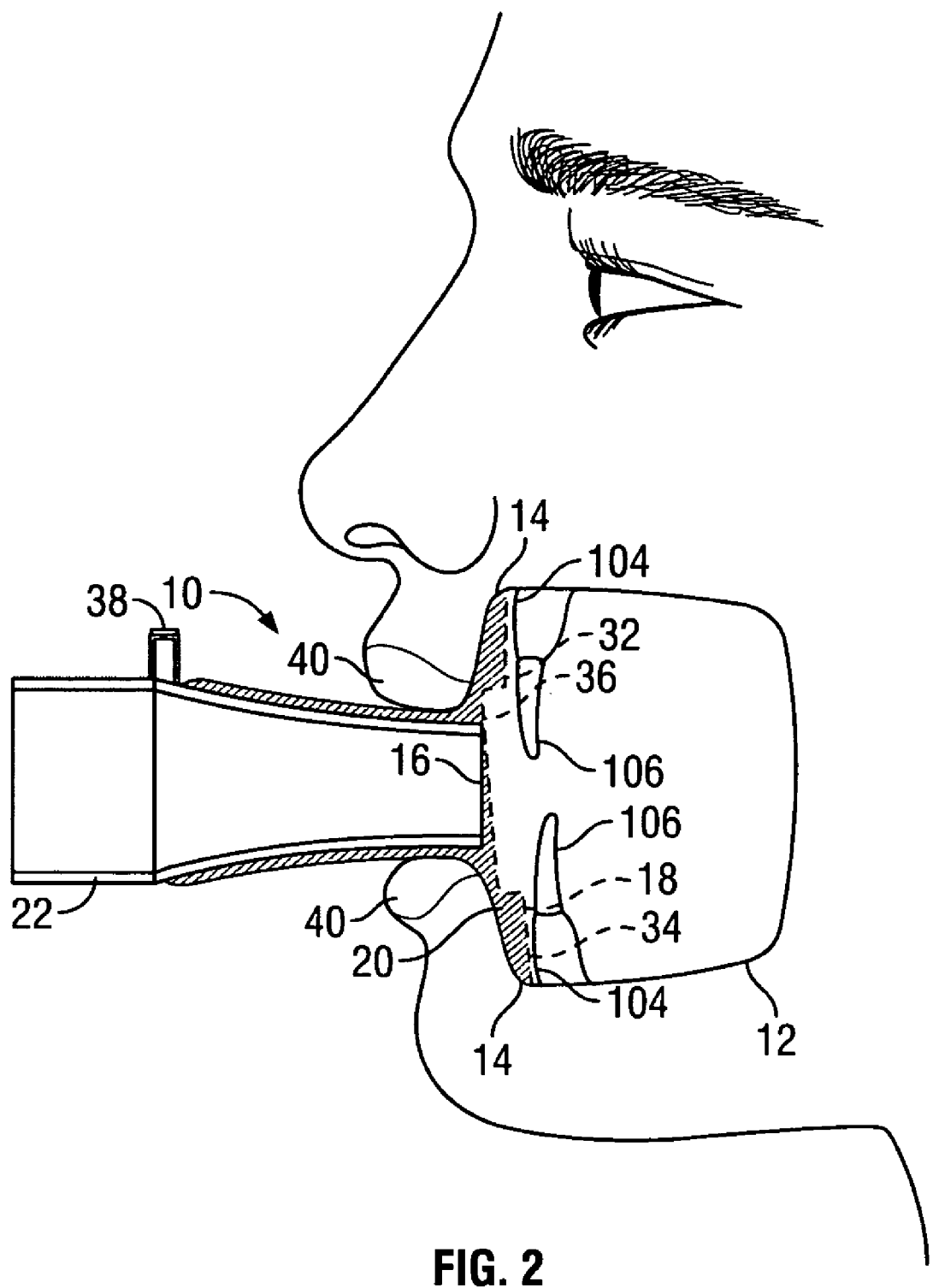
FIG. 2 is a cross-sectional side-view diagram showing a respiratory mask of the present invention inserted in the mouth of a person to be ventilated.

A cross-sectional side-view of the respiratory mask 10 according to an embodiment of the present invention inserted in the mouth of a person to be ventilated is shown in FIG. 2. The sheet of material 14 of the intraoral mouthpiece 12 further comprises a top portion 32 and a bottom portion 34. In an embodiment of the present invention, the top portion 32 of the intraoral mouthpiece 12 is offset from the bottom portion 34 of the intraoral mouthpiece 12 in the anterior-posterior plane so that the respiratory mask 10 fits in mouths of persons with overbites, or, the respiratory mask 10 can be rotated 180° to fit mouths of persons with underbites. This offset enhances comfort of the person to be ventilated as the intraoral mouthpiece 12 fits well against mouths of various geometries. The sheet of material 14 of the intraoral mouthpiece 12 has a recess 36 on the inner surface 18 of the sheet of material 14 to allow the placement of an intraoral oropharyngeal airway as discussed below with respect to FIG. 4.

The tubular extension 22 has an optional port 38 extending therethrough. This port 38 may be used to insert a $CO_2$ probe to monitor respiratory rates in anesthesia use, a pressure relief valve to prevent barotrauma, or other future innovations.

The lips 40, gums 104, and teeth 106 of the person to be ventilated are shown relative to the respiratory mask 10. With the lips 40 closed around the tubular extension 22, the vertical height of the intraoral mouthpiece 12 causes the teeth 106 to remain agape. Therefore, advantageously, the teeth do not present an obstacle to gas flow with the respiratory mask 10 of the present invention.

Figure 3:
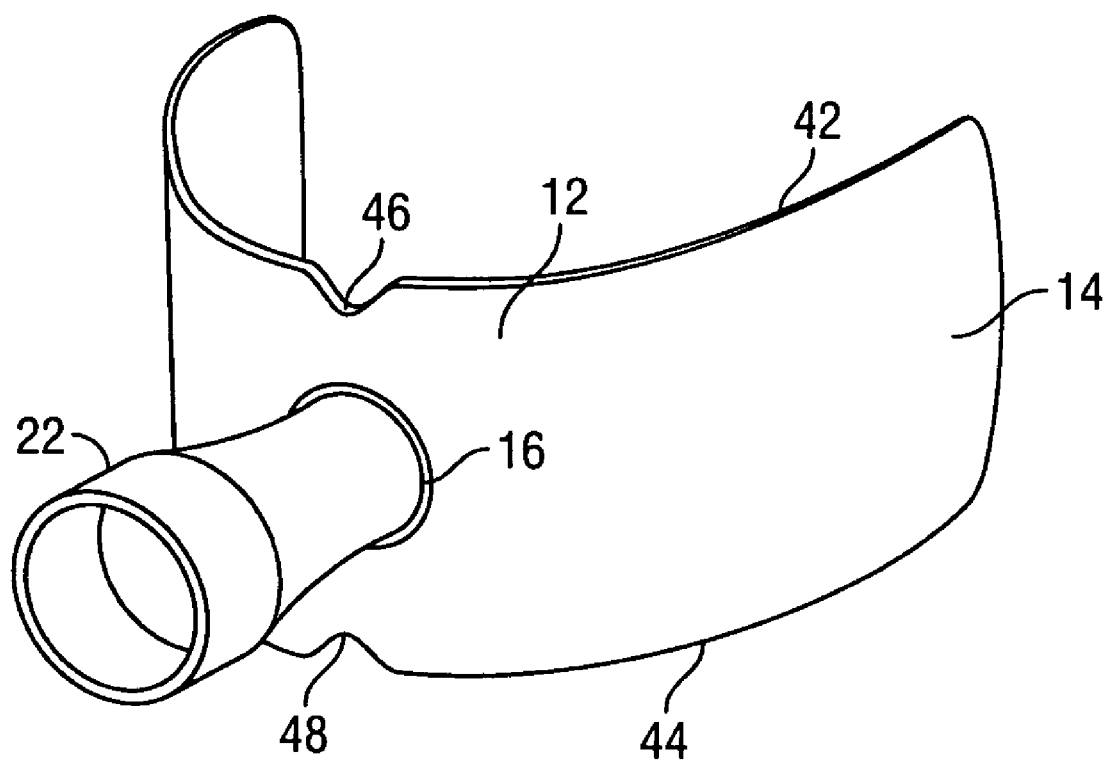
FIG. 3 is an angle view diagram showing a respiratory mask of the present invention.

An angled view of a respiratory mask according to an embodiment of the present invention is shown in FIG. 3. The sheet of material 14 of the intraoral mouthpiece 12 is inserted into the mouth of the ventilated person so that the sheet of material 14 is inside the lips 40 of the ventilated person.

The sheet of material 14 has a top edge 42 and a bottom edge 44. The top edge 42 and the bottom edge 44 of the sheet of material 14 are substantially smooth and rounded to prevent irritation of the lips and gums of the person to be ventilated. To further provide for the comfort of the person to be ventilated, the intraoral mouthpiece further comprises at least one notch 46 and 48. The notch is positioned laterally centered on either the top edge 42 or the bottom edge 44 of the sheet of material 14. The notches 46 and 48 have an open side along the top edge 42 or the bottom edge 44 of the sheet of material 14 and an apex pointing toward the central orifice 16 of the intraoral mouthpiece 12. Preferably, the sheet of material 14 has two notches 46 and 48, both located laterally centered on the sheet of material 14 of the intraoral mouthpiece 14. One of the two notches 46 has its open side along the top edge 42 of the sheet of material 14 and its apex pointed toward the central orifice 16 of the intraoral mouthpiece 12. The other of the two notches has its open side along the bottom edge 44 of the sheet of material 14 and its apex pointed toward the central orifice 16 of the intraoral mouthpiece 12. The notches 46 and 48 reduce or prevent the sheet of material 12 of the intraoral mouthpiece 10 from irritating frenula between the lips and gums of ventilated persons.

Figure 4:
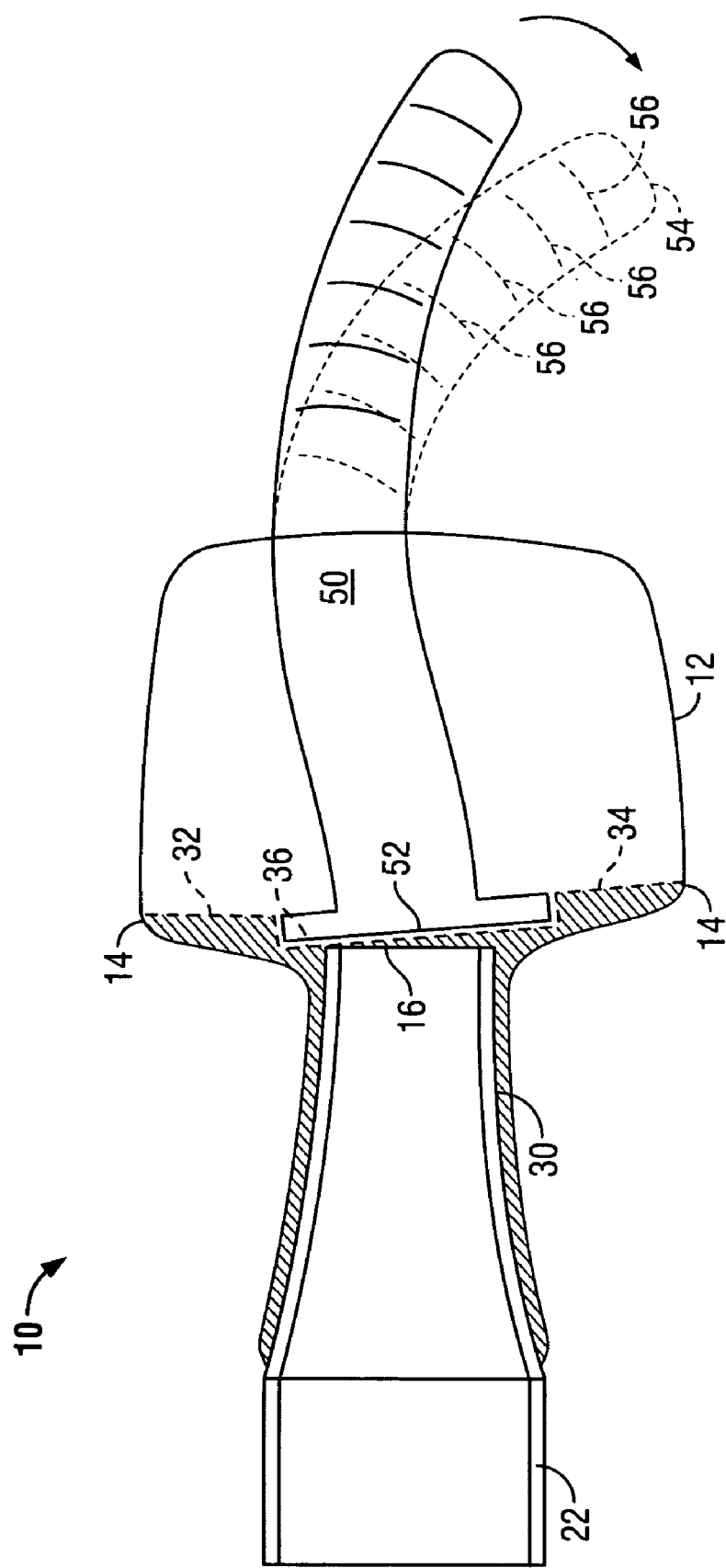
FIG. 4 is a cross-sectional side-view diagram showing a respiratory mask of the present invention with an intraoral oropharyngeal airway.

A cross-sectional side-view diagram of a respiratory mask of an embodiment of the present invention with an intraoral oropharyngeal airway is shown in FIG. 4. The respiratory mask 10 comprises an intraoral oropharyngeal airway 50, an intraoral mouthpiece 12, a tubular extension 22, and a reinforced collar 30. The intraoral oropharyngeal airway prevents the tongue of the person being ventilated from blocking the airway.

The intraoral oropharyngeal airway 50 has a proximal end 52 and a distal end 54. In an embodiment of the present invention, the intraoral oropharyngeal airway has at least one row of notches 56 towards the distal end 54 of the intraoral oropharyngeal airway 50. The row of notches 56 allow the intraoral oropharyngeal airway 50 to flex and follow the shape of the ventilated person's mouth as the intraoral oropharyngeal airway is inserted. Unlike the intraoral oropharyngeal airways of the prior art, this flexion allows the intraoral oropharyngeal airway 50 to be inserted in the mouth of the ventilated person without being rotated and without the use of a tongue blade.

One embodiment of the intraoral oropharyngeal airway 50 is positioned such that the proximal end 52 of the intraoral oropharyngeal airway 50 mates with the recess 36 on the inner surface 18 of the sheet of material 14. The placement of the proximal end 52 of the intraoral oropharyngeal airway 50 in the recess 36 ensures proper fitting of the intraoral mouthpiece 12 without compromising performance and seal.

Figure 5:
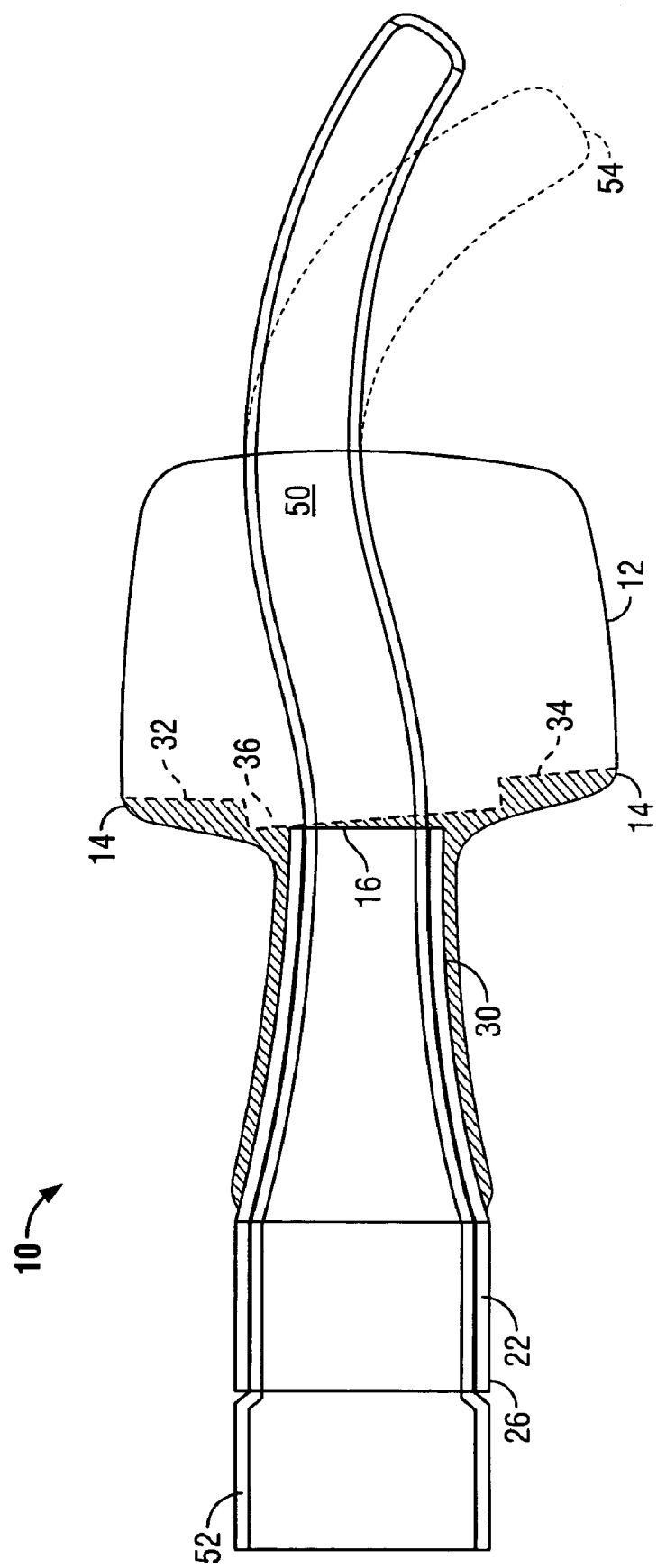
FIG. 5 is a cross-sectional side-view diagram showing a respiratory mask of the present invention with an alternate intraoral oropharyngeal airway.

A cross-sectional side-view diagram of a respiratory mask of the present invention with an alternate intraoral oropharyngeal airway is shown in FIG. 5. The alternate intraoral oropharyngeal airway 50 is slidably inserted through the tubular extension 22 such that the proximal end 52 of the intraoral oropharyngeal airway 50 remains outside the distal end 26 of the tubular extension 22. The proximal end 52 of the intraoral oropharyngeal airway is configured to hold firmly to standard respiratory fittings for a bag valve mask or demand valve.

Figure 6:
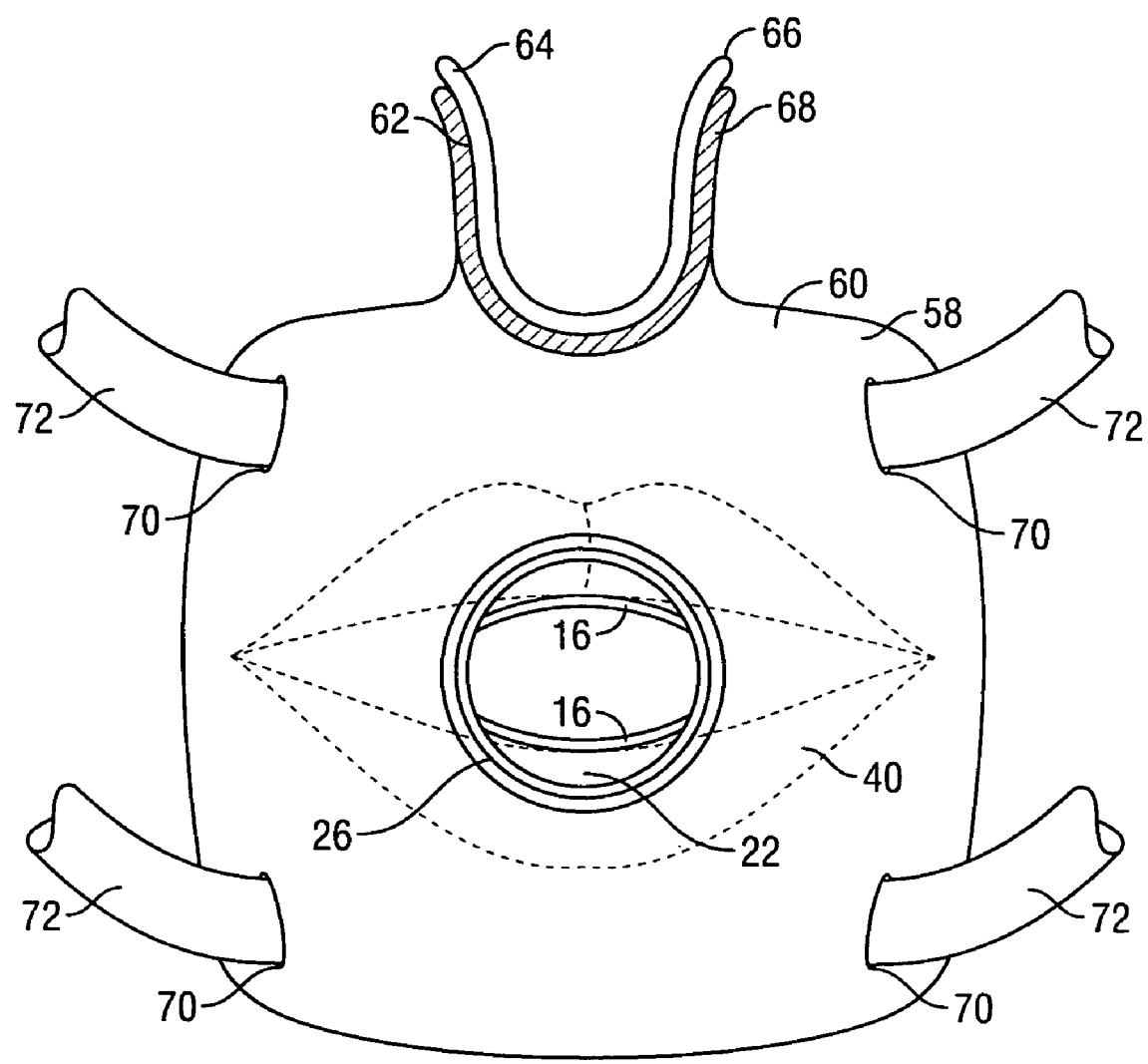
FIG. 6 is an end view diagram showing a respiratory mask of the present invention with an external shield positioned on a ventilated person's face.

FIG. 6 shows an end view diagram of a respiratory mask embodying the present invention with an external shield positioned on the ventilated person's face. In overview the external shield 58 is positioned outside the lips 40 of the ventilated person. The distal end 26 of the tubular extension 22 passes through the external shield 58. The external shield 58 may be removably attached to the respiratory mask 10, or alternatively, the external shield 58 may be affixed to the respiratory mask 10. In an embodiment of the present invention, the external shield 58 is composed of a translucent or transparent material so that vomit, bleeding, emesis or other complications of the ventilated person can be viewed by the healthcare provider while the external shield 58 provides the healthcare provider with barrier protection from the secretions.

A first embodiment of the external shield 58 comprises a shield section 60 and a nasal clamp 62 affixed to the shield section 60. The nasal clamp 62 comprises a first flap 64 positioned to lie adjacent to one nasal opening of the ventilated person, a second flap 66 positioned to lie adjacent to the other nasal opening of the person, and an adjustable reinforcement member such as a malleable band 68 affixed to the first flap 64 and the second flap 66. The malleable band 68 reinforces the first flap 64 and the second flap 66 so that the nasal clamp 62 can be pinched together to close off the nostrils of the ventilated person to prevent the leakage of gas. Therefore, unlike prior art respiratory masks, the integrated nasal clamp 62 of the present invention essentially eliminates gas leakage through the nose of the person being ventilated. In alternate embodiments of the nasal clamp, the adjustable reinforcement member, depicted here as a malleable band 68, may be a ratcheted clamp or other similar device.

The external shield 58 has a plurality of slits 70 configured to admit at least one external shield restraining strap 72. The external shield 58 provides padding to the face of the ventilated person when pressure is applied to the present invention to reduce gas leakage. Pressure may be applied to the present invention by a direct application of pressure by the hand of a healthcare provider, or by tightening the external shield restraining strap 72 around the head of the ventilated person. Additionally, the external shield 58 provides an additional layer of gas sealing in respiratory masks of the present invention, preventing gas leakage when respiratory masks of the present invention are used on apneic, sedated, or unconscious persons. The nasal clamp 62 and the shield section 60 may be grooved or sticky in order to enhance traction despite exposure to various bodily fluids, cosmetics, facial hair, or injury.

Figure 7A:
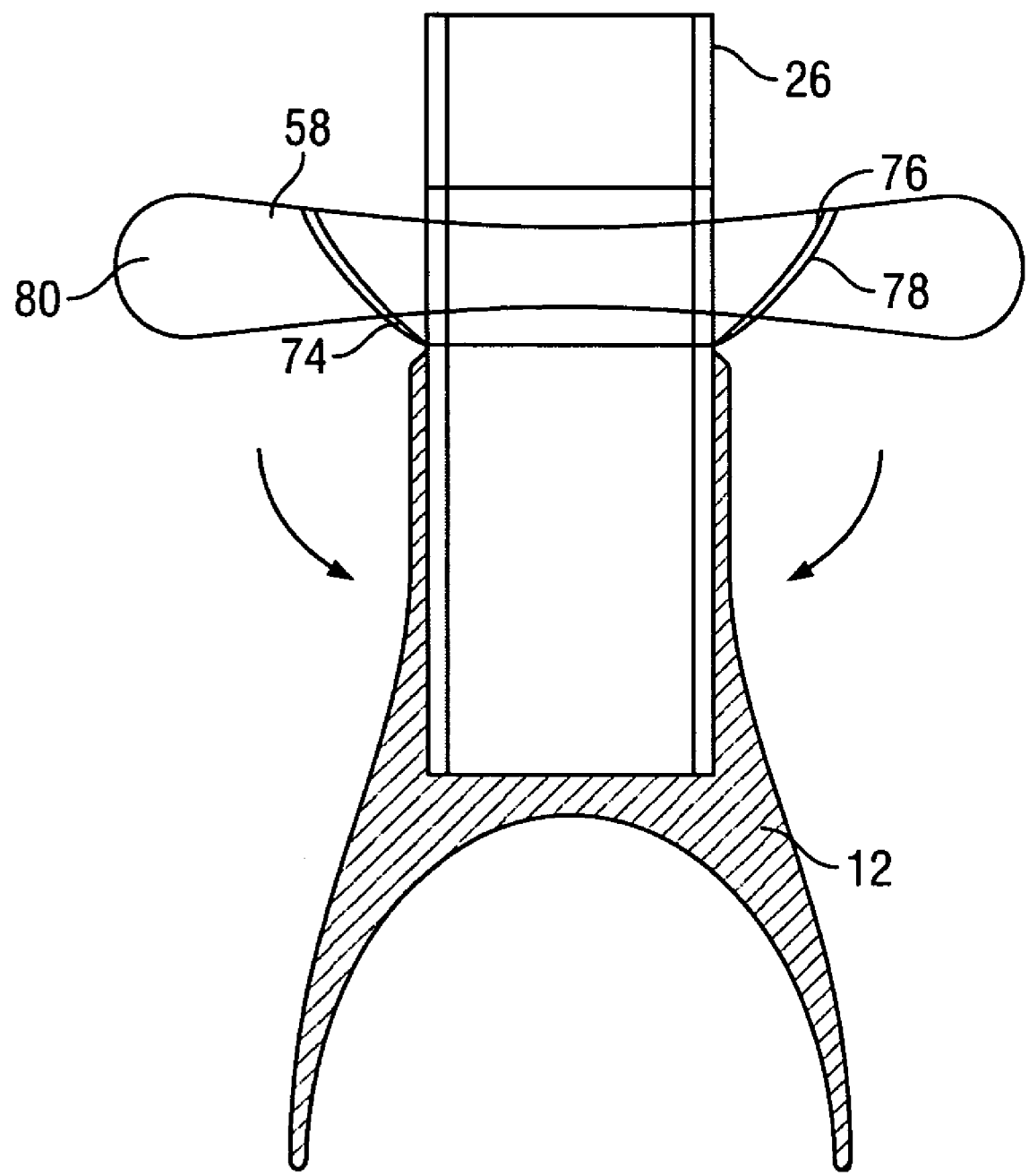
FIG. 7A is a cross-sectional top-view diagram showing a respiratory mask of the present invention with an invertible domed face shield in an inverted position.
Figure 7B:
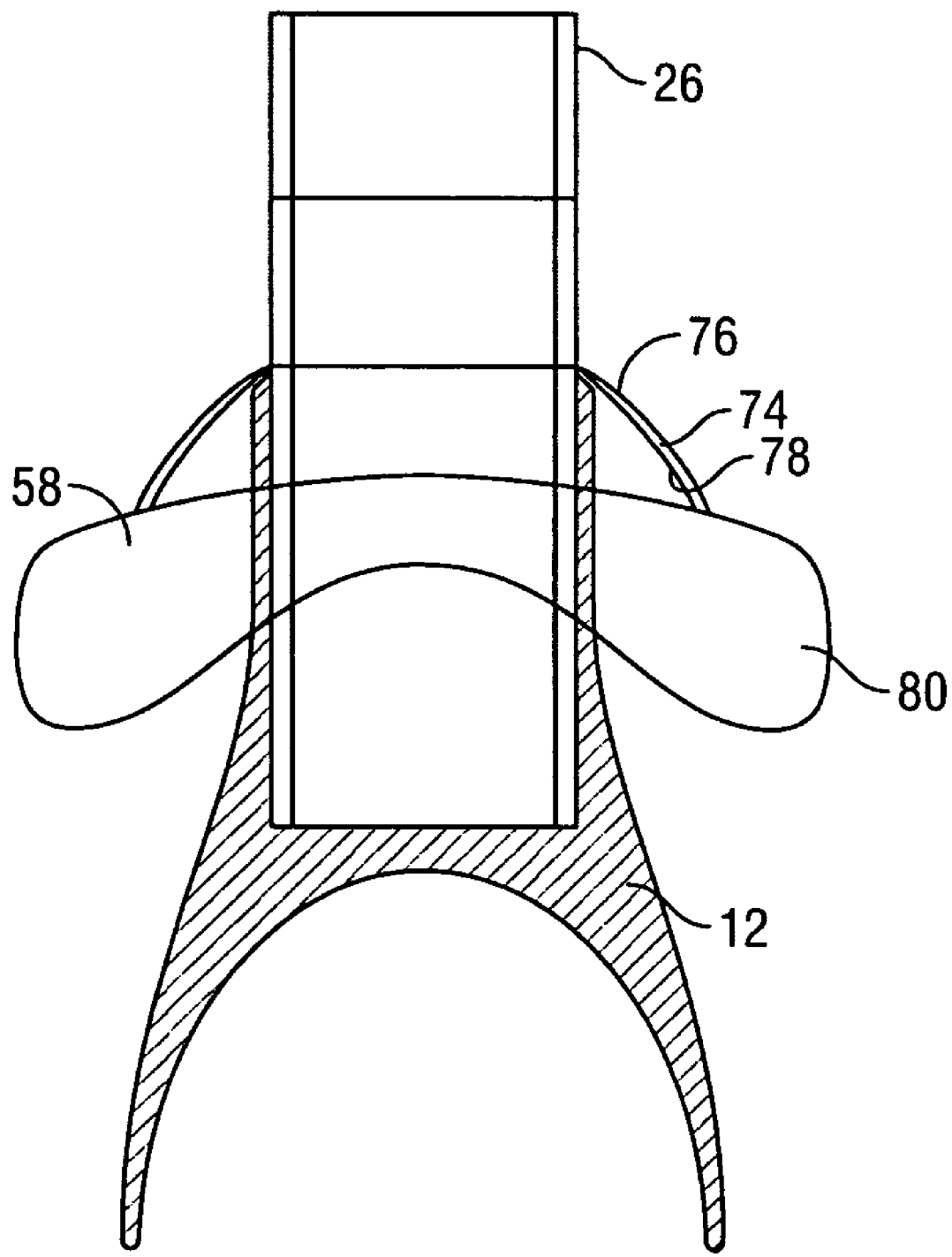
FIG. 7B is a cross-sectional top-view diagram showing a respiratory mask of the present invention with an invertible domed face shield in an everted position.

FIG. 7 depicts a cross-sectional top-view diagram showing a respiratory mask of the present invention with a second embodiment of the external shield. The second embodiment of the external shield 58 is comprised of a substantially oval invertible domed face shield 74 and padding 80. The substantially oval invertible domed face shield 74 has an outer side 76 and an inner side 78. The padding 80 is affixed to the inner side 78 of the substantially oval invertible (with respect to the wearer's face) domed face shield 74. The substantially oval invertible domed face shield 74 is substantially oval-shaped with a longer horizontal axis adapted to mimic the shape of a person's mouth. In an embodiment of the present invention, the padding 80 may be composed of a soft, silicon-like material or air cushion to conform to the ventilated person's facial features. FIG. 7A depicts the substantially oval invertible domed face shield 74 in an inverted position. FIG. 7B depicts the substantially oval invertible domed face shield 74 in an everted position. The substantially oval invertible domed face shield 74 can be in the inverted position prior to insertion of the respiratory mask into the ventilated person's mouth, then everted to provide a seal once the respiratory mask has been inserted into the ventilated person's mouth. The everted position of the domed mask can also provide additional gentle inward pressure on the face to reduce the need for the provider to press excessively. In certain embodiments of the present invention, the substantially oval invertible domed face shield 74 may comprise a nasal clamp 62 of the types depicted in FIG. 6 or 8 and slits 70 as depicted in FIG. 6.

FIG. 8 depicts a respiratory mask embodying the present invention with the external shield 58 including a nasal mask 82. In this embodiment of the present invention, the nasal clamp 62 comprises a nasal mask 82 having a first side 84 and a second side 86, padding 88, and an adjustable reinforcement member such as a malleable band 90. The nasal mask 82 covers a lower portion of the ventilated person's nose. The padding 88 of the nasal mask 82 is affixed to the first side 84 of the nasal mask 82 such that when the nasal mask 82 is firmly placed on the nose of a ventilated person, the padding 82 will force the nostrils of the ventilated person to close off. The malleable band 90 reinforces the nasal mask 82. In alternate embodiments of the nasal mask, the adjustable reinforcement member, depicted here as a malleable band 90, may be a ratcheted clamp or other similar device.

Figure 8A:
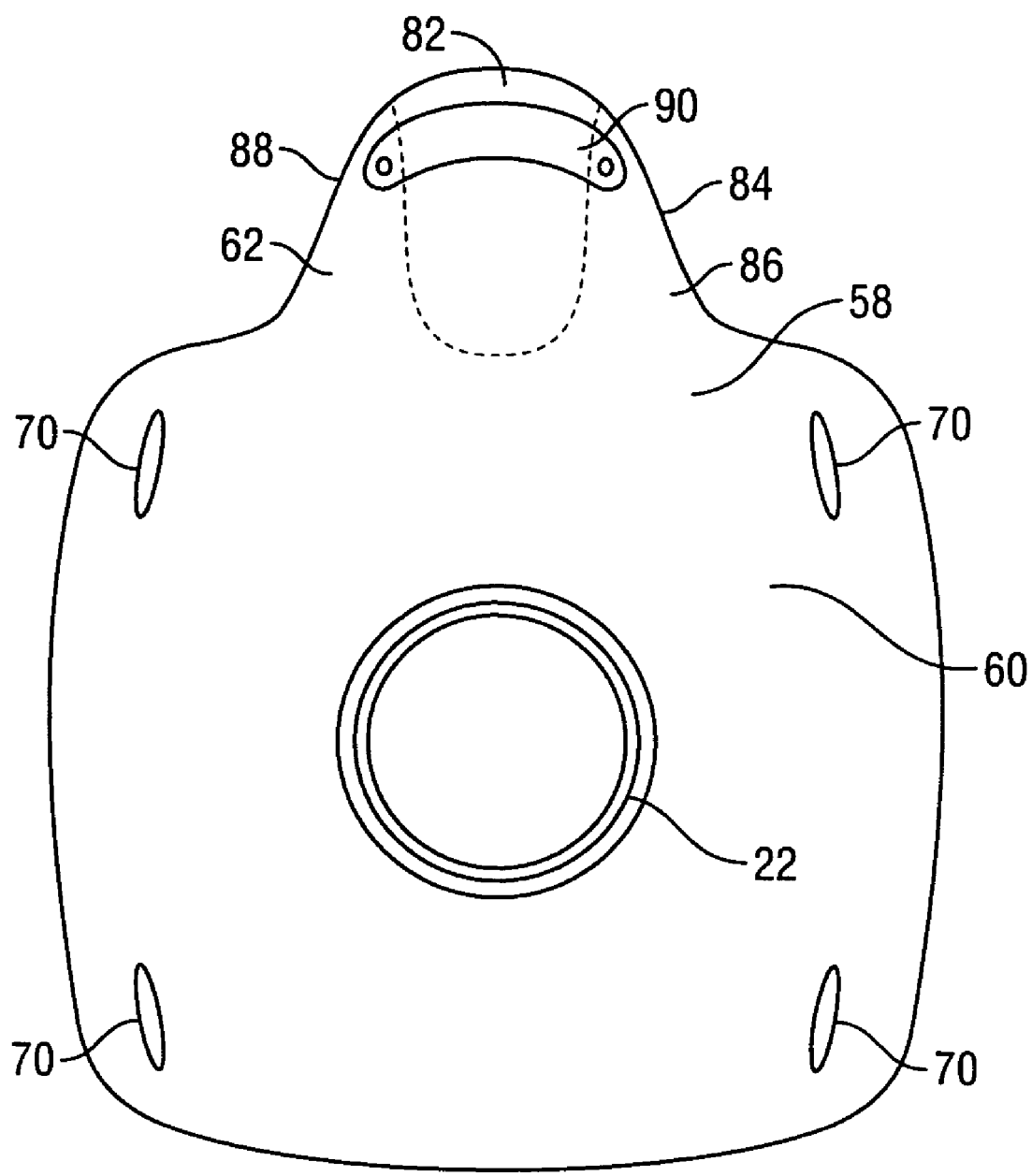
FIG. 8A is an end-view diagram showing a respiratory mask of the present invention with an embodiment for an exterior shield including a nasal mask.
Figure 8B:
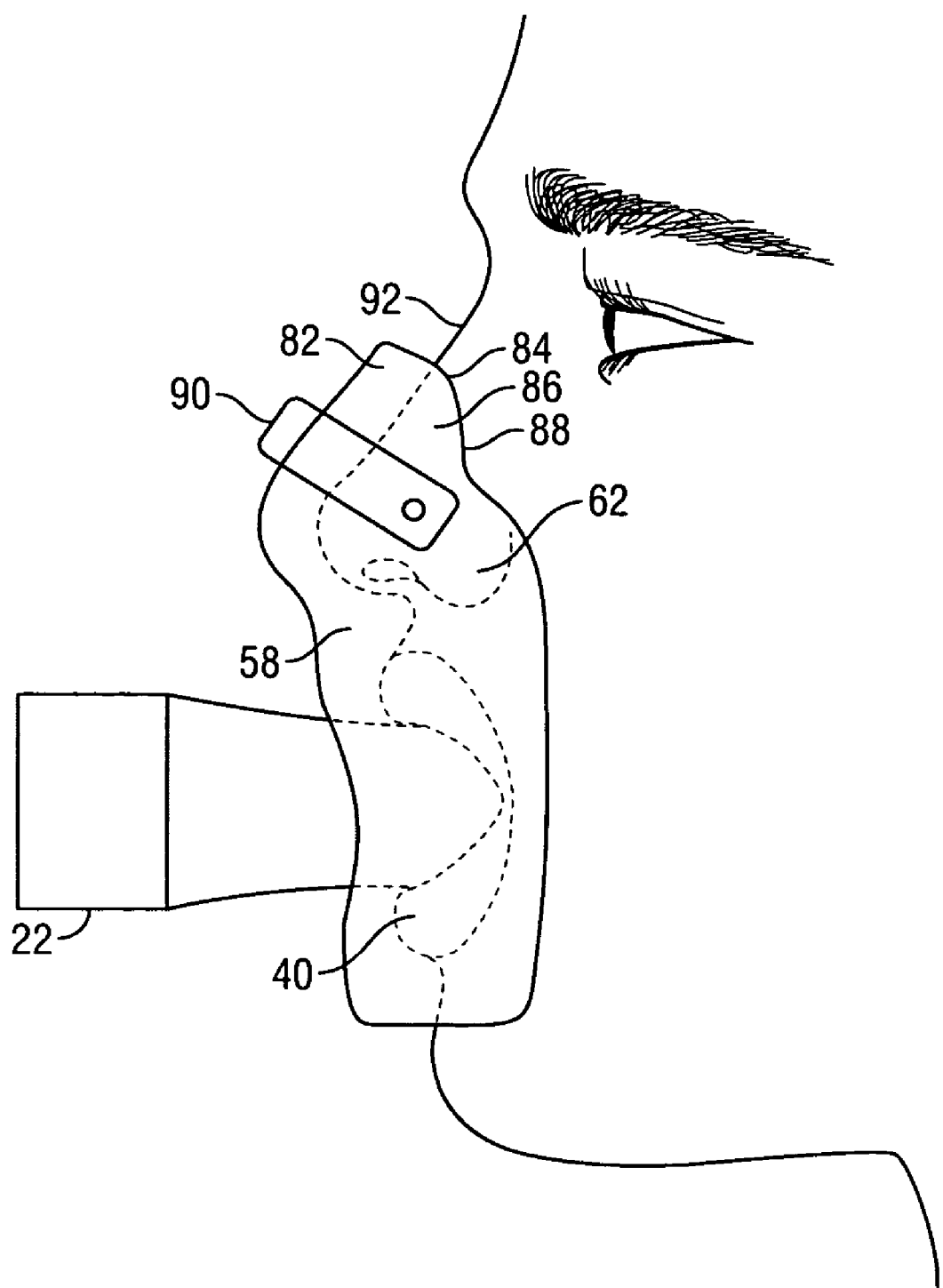
FIG. 8B is a side-view diagram showing the respiratory mask of FIG. 8A positioned in a ventilated person's mouth.

FIG. 8A is an end view diagram of an embodiment of the present invention with an external shield 60 and a nasal mask 82. FIG. 8B is a side view diagram depicting an embodiment of the present invention with an external shield 60 and nasal mask 82 positioned over the lips 40 and nose 92 of a ventilated person.

Figure 9:
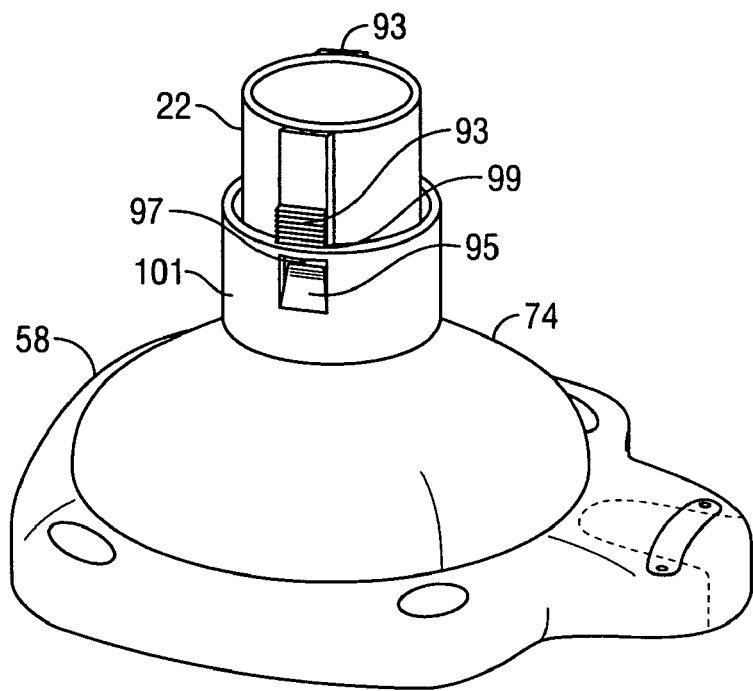
FIG. 9 is a side-view diagram showing a respiratory mask of the present invention with an invertible domed face shield that is removably attached to the respiratory mask with a locking mechanism.

FIG. 9 is a side view diagram of an embodiment of the present invention with a substantially oval invertible domed face shield that is removably attached to the tubular extension of the respiratory mask. The external shield 58, here depicted as a substantially oval invertible domed face shield 74 has a mating collar 101 to slidably engage the tubular extension 22 of the respiratory mask. A multi-position locking mechanism 97 allows the external shield 58 to be adjustably secured with respect to the tubular extension 22. The multi-position locking mechanism 97 depicted in this figure comprises two rows of detents 93 positioned radially opposed on the outside of the tubular extension 22 and two stops 95 positioned radially opposed on the inner surface of the mating collar 101 of the external shield 58. To provide proper alignment of the external shield 58 with the respiratory mask, the rows of detents 93 are slightly raised relative to the tubular extension 22 and mate with recesses 99 in the mating collar 101. The position of the external shield 58 can thus be varied and secured with respect to the tubular extension 22 by placing the stops 95 in various detents 93.

The position of the multi-position locking mechanism can be adjusted by squeezing the mating collar 101 offset from the stops 95 and the detents 93 to release the stops 95 from the detents 93. While this multi position locking mechanism is depicted, multiple arrangements of these elements (for example, alternatively, the stops 95 could be located on the tubular extension 22 and the detents 93 could be located on the mating collar 101) could provide similar functionality. Additionally, several types of multi-position locking mechanisms are known in the art and are considered to be within the scope of the present invention. For example, the multi-position locking mechanism may use a lock screw, a locking pin inserted through one of several holes or recesses, a spring loaded integral pin mating with one of several holes or recesses, or other arrangement to adjustably secure the external shield 58 relative to the tubular extension 22.

Figure 10:
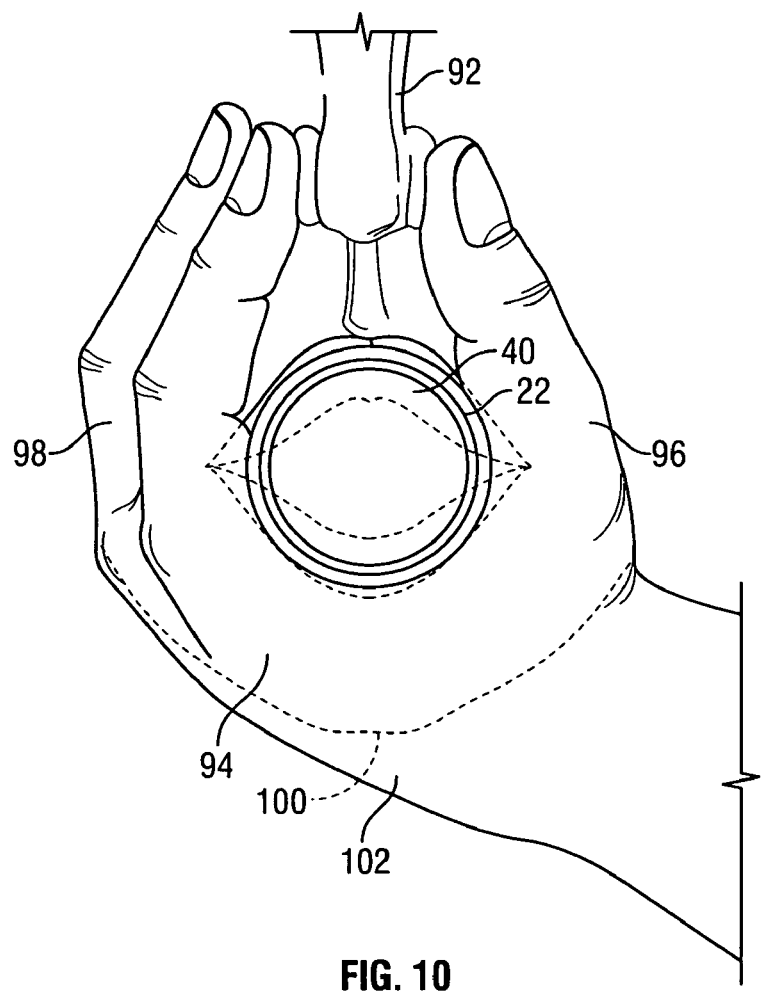
FIG. 10 is an end-view diagram showing a respiratory mask of the present invention positioned in a ventilated person's mouth with a hand of a healthcare provider positioned to enhance sealing between the respiratory mask and the mouth of the ventilated person.

FIG. 10 depicts a respiratory mask of the present invention positioned in the ventilated person's mouth with a hand of a healthcare provider positioned to enhance gas sealing between the respiratory mask and the mouth of the ventilated person without the use of the external shield. The hand 94 of the healthcare provider is positioned such that the thumb 96, palm 102, and fingers 98 of the hand 94 form an approximate "u" shape characterized by a base and two sides. The thumb 96 and fingers 98 form the two sides of the "u" shape and are positioned on either side of the openings of the nose 92 of the ventilated person. The palm 102 of the hand 94 of the healthcare provider forms the base of the "u" shape and lies below the tubular extension 22 over an area between the lips 40 and the chin 100 of the ventilated person resting in the palm of the provider's hand. This hand positioning can more readily hyperextend the wearer's head to improve the airway opening, similar to the commonly known head-tilt-chin-lift method. The provider's hand can relax during exhalation to ease the gases exiting from the wearer's lungs and airways.

The healthcare provider reduces gas leaks to a ventilated person with the present invention by inserting a respiratory mask of the present invention into the mouth of a person to be ventilated, positioning one hand 94 of the healthcare provider in the "u" shape depicted in FIG. 10, applying pressure with the hand 94 onto the face of the ventilated person pressing the lips 40 toward the gums of the ventilated person, and squeezing the nose 92 of the ventilated person with the thumb 96 and at least one of the fingers 98. In this manner, the healthcare provider can provide gas sealing in respiration with any of the embodiments of the present invention using only a single hand. The healthcare provider's other hand is available for ventilation. This handgrip technique in conjunction with the respiratory mask of the present invention represents a marked achievement over the prior art traditional respiratory mask which frequently requires two healthcare providers to adequately ventilate a person and can cause the person facial irritation and discomfort.

Alternatively, the use of an external shield in ventilation can assist in preventing leakage by applying pressure onto the face with the operator's hand or the use of the invertible dome shield. In addition, the use of restraining straps to keep the external shield affixed to the face of the wearer can allow for hands-free ventilation especially during extended use as in transport or anesthesia.

It should be apparent to those skilled in the art that the multiple alternative embodiments of the respiratory mask of the present invention can be made by combining the intraoral mouthpiece and tubular extension of the present invention with: either of the embodiments of the intraoral oropharyngeal airway or no intraoral oropharyngeal airway, either of the embodiments of the external shield or no external shield, and either embodiment of the nasal clamp or no nasal clamp. Having thus described several embodiments of the respiratory mask, it should be apparent to those skilled in the art that certain advantages of the within device have been achieved. It should also be appreciated that various modifications, adaptations, and alternative embodiments thereof may be made within the scope and spirit of the present invention. The invention is further defined by the following claims.

What is claimed is:

1. A respiratory mask, comprising:
   an intraoral mouthpiece comprising:
      a substantially oval and bowed sheet of material having an inner surface, an outer surface, a top portion, a bottom portion, an upper edge, and a lower edge;
      a central orifice through the approximate center of the substantially oval and bowed sheet of material;
   a tubular extension having a proximal end, a distal end, and a conduit, wherein the conduit of the tubular extension at the proximal end of the tubular extension feeds into the central orifice of the intraoral mouthpiece, the proximal end of the tubular extension terminating substantially coextensive with the inner surface of the sheet of material; and
   a reinforced collar surrounding a portion of the tubular extension; and
   wherein the substantially oval and bowed sheet of material is configured to fit between gums and lips of a person, extending upward and downward substantially parallel to the gums and teeth of the person beyond the gumline of the person, and extending posteriorly in the mouth of the person.

2. The respiratory mask of claim 1, wherein the intraoral mouthpiece further comprises at least one notch having an open side and an apex positioned so that the open side of the at least one notch is laterally centered on an edge of the substantially oval and bowed sheet of material and the apex is pointed toward the central orifice through the intraoral mouthpiece.

3. The respiratory mask of claim 1, wherein the top portion of the sheet of material is offset in an anterior-posterior plane with respect to the bottom portion of the intraoral mouthpiece.

4. The respiratory mask of claim 1, further comprising a port extending through the tubular extension.

5. The respiratory mask of claim 1, wherein the inner and outer surfaces of the substantially oval and bowed sheet of material of the intraoral mouthpiece are substantially smooth, and the upper and lower edges of the substantially oval and bowed sheet of material are substantially rounded.

6. The respiratory mask of claim 1, wherein the intraoral mouthpiece is comprised of plastic, rubber, or silicone.

7. The respiratory mask of claim 1, further comprising an intraoral oropharyngeal airway having a proximal end and a distal end wherein the intraoral oropharyngeal airway provides an extension of the conduit of the tubular extension into the mouth of the person.

8. The respiratory mask of claim 7, wherein the intraoral oropharyngeal airway has at least one row of notches towards the distal end of the intraoral oropharyngeal airway.

9. The respiratory mask of claim 7, wherein the intraoral mouthpiece further comprises a recess on the inner surface of the sheet of material, said recess configured to mate with the proximal end of the intraoral oropharyngeal airway and wherein the intraoral oropharyngeal airway is positioned such that the proximal end of the intraoral oropharyngeal airway mates with the recess on the sheet of material.

10. The respiratory mask of claim 7, wherein the intraoral oropharyngeal airway is slidably inserted into the distal end of the tubular extension of the respiratory mask such that the proximal end of the intraoral oropharyngeal airway is positioned outside the distal end of the tubular extension.

11. A respiratory mask, comprising:
a substantially bowed, intraoral mouthpiece comprising an inner surface, an outer surface, a top portion, a bottom portion, an upper edge, and a lower edge, the mouthpiece extending between a first lateral edge and a second lateral edge, the mouthpiece defining a central orifice through an approximate center of the first and second lateral edges; and
a tubular extension having a proximal end, a distal end, and a conduit, wherein the conduit of the tubular extension at the proximal end of the tubular extension feeds into the central orifice of the mouthpiece, the proximal end of the tubular extension terminating substantially coextensive with the inner surface of the mouthpiece;
wherein the mouthpiece is configured to fit between a person's gums and lips, extends upward and downward substantially parallel to the gums and teeth of the person, and extends posteriorly in the person's mouth.

12. The respiratory mask of claim 11, wherein the mouthpiece further comprises a notch having an open side and an apex positioned so that the open side of the notch is laterally centered on the upper edge of the mouthpiece and the apex is pointed toward the central orifice of the mouthpiece.

13. The respiratory mask of claim 11, wherein the mouthpiece further comprises a notch having an open side and an apex positioned so that the open side of the notch is laterally centered on the lower edge of the mouthpiece and the apex is pointed toward the central orifice of the mouthpiece.

14. The respiratory mask of claim 11, wherein the top portion of the mouthpiece is offset in an anterior-posterior plane with respect to the bottom portion of the mouthpiece.

15. The respiratory mask of claim 11, further comprising a port extending through the tubular extension.

16. The respiratory mask of claim 11, wherein the inner and outer surfaces of the mouthpiece are substantially smooth, and the upper and lower edges of the mouthpiece are substantially rounded.

17. The respiratory mask of claim 11, wherein the mouthpiece is comprised of plastic, rubber, or silicone.

18. The respiratory mask of claim 11, further comprising a separable intraoral oropharyngeal airway having a proximal end and a distal end, the airway being adapted to couple to the tubular extension into the mouth of the person.

19. The respiratory mask of claim 18, wherein the airway has at least one row of notches towards the distal end of the airway.

20. The respiratory mask of claim 18, wherein the mouthpiece further comprises a recess on the inner surface, the recess configured to receive the proximal end of the airway, the airway being positioned such that the proximal end of the airway mates with the recess on the mouthpiece.

21. The respiratory mask of claim 11, wherein the mouthpiece has a shape adapted to conform to an inner surface of the gums and lips of the person.

22. The respiratory mask of claim 11, further comprising a reinforced collar that surrounds a portion of the tubular extension.

23. The respiratory mask of claim 11, wherein the mouthpiece has a substantially oval shape.

24. A respiratory mask, comprising:
a substantially bowed, intraoral mouthpiece comprising an inner surface, an outer surface, a top portion, a bottom portion,. an upper edge, and a lower edge, the mouthpiece extending between a first lateral edge and a second lateral edge, the mouthpiece defining a central orifice through an approximate center of the first and second lateral edges; and
a tubular extension having a proximal end, a distal end, and a conduit, wherein the conduit of the tubular extension at the proximal end of the tubular extension feeds into the central orifice of the mouthpiece;
wherein the mouthpiece is configured to fit between a person s gums and lips, extends upward and downward substantially parallel to the gums and teeth of the person, and extends posteriorly in the person's mouth; and
wherein a first lateral portion of the mouthpiece between the central orifice and the first lateral edge provides lateral flexibility, and a second lateral portion of the mouthpiece between the central orifice and the second lateral edge also provides lateral flexibility, thereby facilitating introduction and removal of the mouthpiece from the patient's mouth.

25. The respiratory mask of claim 24, wherein the mouthpiece further comprises a notch having an open side and an apex positioned so that the open side of the notch is laterally centered on the upper edge of the mouthpiece and the apex is pointed toward the central orifice of the mouthpiece.

26. The respiratory mask of claim 24, wherein the mouthpiece further comprises a notch having an open side and an apex positioned so that the open side of the notch is laterally centered on the lower edge of the mouthpiece and the apex is pointed toward the central orifice of the mouthpiece.

27. The respiratory mask of claim 24, wherein the top portion of the mouthpiece is offset in an anterior-posterior plane with respect to the bottom portion of the mouthpiece.

28. The respiratory mask of claim 24, further comprising a port extending through the tubular extension.

29. The respiratory mask of claim 24, wherein the inner and outer surfaces of the mouthpiece are substantially smooth, and the upper and lower edges of the mouthpiece are substantially rounded.

30. The respiratory mask of claim 24, wherein the mouthpiece is comprised of plastic, rubber, or silicone.

31. The respiratory mask of claim 24, further comprising a separable intraoral oropharyngeal airway having a proximal end and a distal end, the airway being adapted to couple to the tubular extension into the mouth of the person.

32. The respiratory mask of claim 31, wherein the airway has at least one row of notches towards the distal end of the airway.

33. The respiratory mask of claim 31, wherein the mouthpiece further comprises a recess on the inner surface, the recess configured to receive the proximal end of the airway, the airway being positioned such that the proximal end of the airway mates with the recess on the mouthpiece.

34. The respiratory mask of claim 24, wherein the mouthpiece has a shape adapted to conform to an inner surface of the gums and lips of the person.

35. The respiratory mask of claim 24, further comprising a reinforced collar that surrounds a portion of the tubular extension.

36. The respiratory mask of claim 24, wherein the mouthpiece has a substantially oval shape.

* * * * *